(12) United States Patent  (10) Patent No.: US 7,136,221 B2
Strobel et al.  (45) Date of Patent: Nov. 14, 2006

(54) MICROSCOPE WITH A HANDLE AND/OR HAND-GRIP FOR A MICROSCOPE

(75) Inventors: Peter Strobel, St. Gallen (CH); Fritz Sollberger, Bauma (CH)

(73) Assignee: Leica Microsystems (Switzerland) AG, Heerbrugg (CH)

( * ) Notice: Subject to any disclaimer, the term of this patent is extended or adjusted under 35 U.S.C. 154(b) by 0 days.

(21) Appl. No.: 09/956,246

(22) Filed: Sep. 20, 2001

(65) Prior Publication Data

US 2003/0053203 A1 Mar. 20, 2003

(30) Foreign Application Priority Data

Sep. 22, 2000 (CH) .................................. 1897/00

(51) Int. Cl.
G02B 21/10 (2006.01)
F16M 11/04 (2006.01)
G05G 1/12 (2006.01)
A47J 45/00 (2006.01)
F16K 35/02 (2006.01)

(52) U.S. Cl. ................. 359/368; 359/384; 248/123.11; 74/528

(58) Field of Classification Search ........ 359/368–390, 359/808–819, 400–409, 900; 74/528, 548; 248/123.11; 292/352
See application file for complete search history.

(56) References Cited

U.S. PATENT DOCUMENTS

| 4,577,367 | A |   | 3/1986 | Durand ........................ 16/114 |
| 5,121,655 | A |   | 6/1992 | Toshimitsu ................ 74/665 B |
| 5,343,776 | A | * | 9/1994 | Falco et al. .................... 74/558 |
| 5,694,815 | A | * | 12/1997 | Biber et al. .................... 74/528 |
| 5,844,714 | A | * | 12/1998 | DiResta ........................ 359/368 |
| 5,861,983 | A |   | 1/1999 | Twisselman ................. 359/384 |
| 5,887,850 | A | * | 3/1999 | Ruffalo .......................... 251/95 |
| 5,891,020 | A |   | 4/1999 | Luber et al. ................. 600/300 |
| 6,110,190 | A | * | 8/2000 | Ginn et al. .................. 606/190 |
| 6,434,416 | B1 |   | 8/2002 | Mizoguchi et al. ......... 600/427 |
| 6,471,165 | B1 | * | 10/2002 | Twisselmann .......... 248/123.11 |
| 6,592,086 | B1 | * | 7/2003 | Sander .................... 248/123.11 |
| 2002/0014562 | A1 |   | 2/2002 | Twisselmann .......... 248/123.11 |

FOREIGN PATENT DOCUMENTS

| DE | 196 40 993 A1 | 4/1997 |
| FR | 2 541 573 A1 | 8/1984 |
| JP | 2000-139949 A | 5/2000 |
| JP | 2001-120573 A | 5/2001 |

* cited by examiner

Primary Examiner—Thong Q Nguyen
(74) Attorney, Agent, or Firm—Foley & Lardner LLP

(57) ABSTRACT

The invention relates to a hand-grip with a grip part which can be detachably fastened on a microscope housing, the mounting and dismounting being possible with a single-handed movement with the gripping hand. The hand-grip is fashioned and positioned such that it permits operation of the microscope in all directions with only one hand.

48 Claims, 3 Drawing Sheets

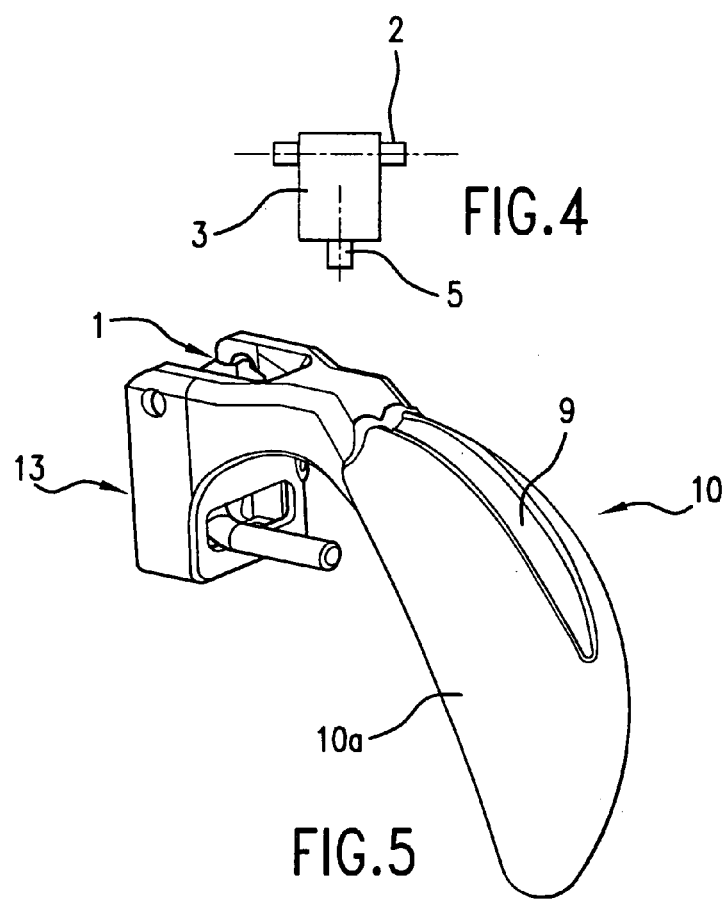
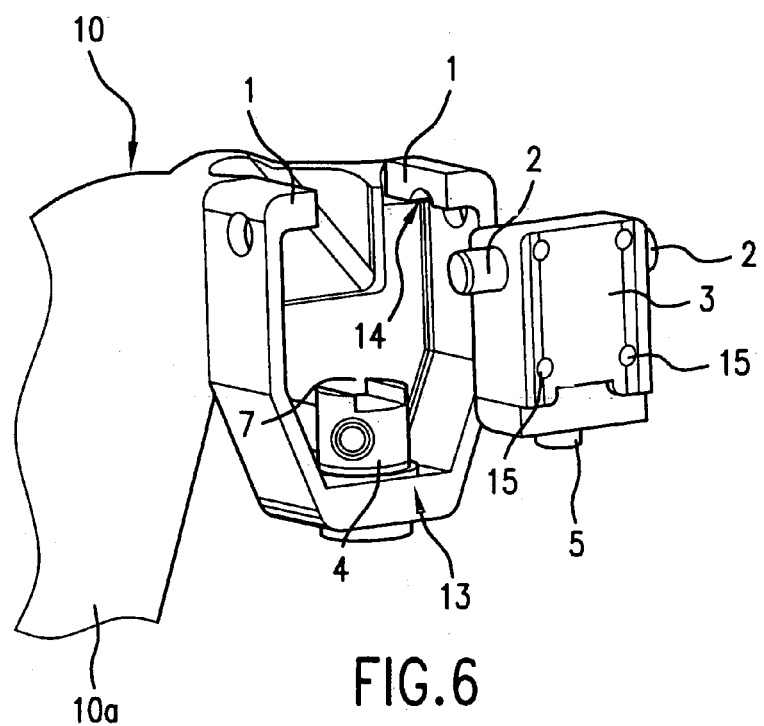

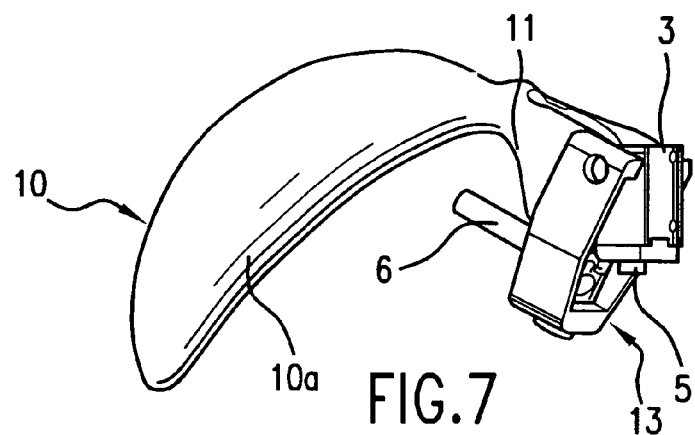
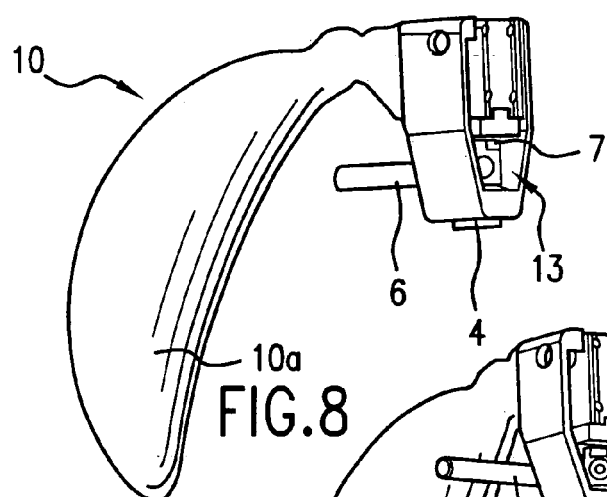
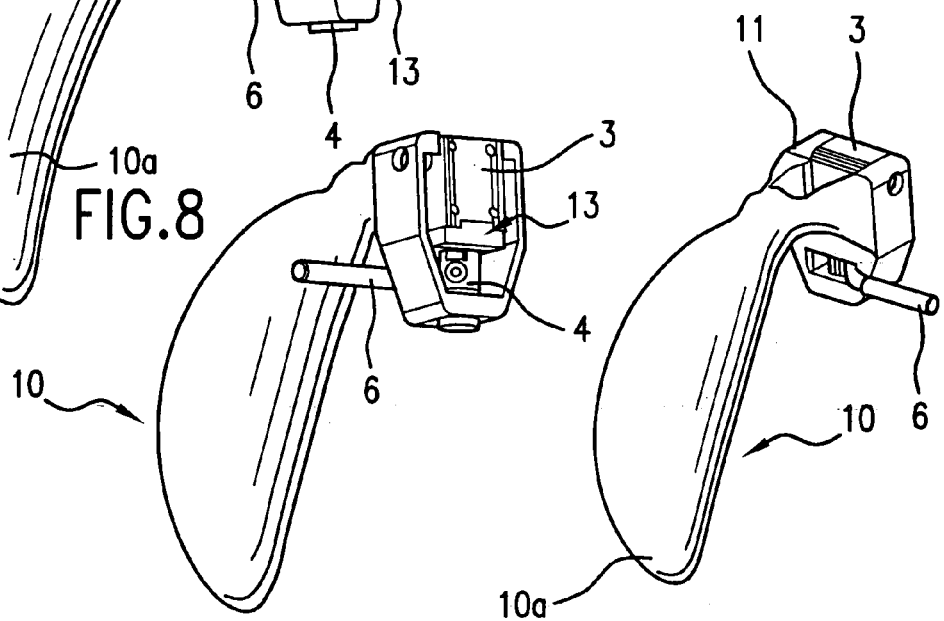
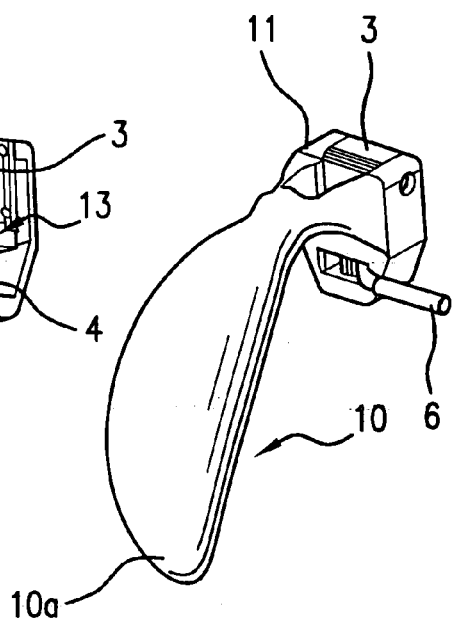

MICROSCOPE WITH A HANDLE AND/OR HAND-GRIP FOR A MICROSCOPE

CROSS REFERENCE TO RELATED APPLICATIONS

This invention claims priority of the Swiss patent application 1897/00 which is incorporated by reference herein.

FIELD OF THE INVENTION

The invention relates to the hand-grip on a microscope—from the type of fastening on the microscope housing, on the one hand, and from the number of fastening locations and the location of fastening on the microscope, on the other hand.

In particular, the invention relates to a hand-grip for a microscope which can be fitted in an ergonomic and comfortable way on a microscope which is suspended on a suitable moving stand such that the microscope can also be moved under sterile conditions in space. Such movements include up/down, forward/back, sideways, rotate, pivot, incline, etc.

BACKGROUND OF THE INVENTION

Conventional hand-grips have become known in the most varied forms and mounting types. They are mostly screw in pairs (left and right) on the microscope housing, or constructed on rods which are fastened on the pivoted support of a microscope and therefore move the latter only indirectly.

When controlling a microscope, the user lays his two hands on the gripping pieces of conventional hand-grips, and, if appropriate, actuates electric switches or the like, in order to release brakes or the like, and then moves the microscope by muscular force to the desired position. In the case of particularly smoothly mounted microscopes such as, for example, surgical microscopes on a special stand (OHS) from the applicant, skilled users can carry out most movements of the microscope even with one hand, since the electric switching elements are arranged on both hand-grips-handgrips on both the left and right side.

In a fashion comparable to a motor bicycle handlebar—the pairwise hand-grips frequently extend horizontally so that a user can apply the microscope between his spread hands.

However, this disadvantageously results in space being used by the hand-grips which would otherwise be free. Chiefly, in the case of built-on accessories with assistant terminals, this leads to space problems for assistants. Above all, the hand-grips fastened on rods disadvantageously increase the overall weight of the microscope structure which must be borne by the stand.

SUMMARY OF THE INVENTION

It is therefore the object of the invention to find an improved grip arrangement or configuration which avoids the problems mentioned.

This object is achieved by means seen in the present specification. The replacement of two hand-grips by one hand-grip which is fitted, or can be detachably fitted, at a central point of the microscope body and extends in at least two space directions of the coordinate system, leads firstly to a substantial weight reduction, and secondly to the possibility of operating the microscope with only one hand. The space problems mentioned for the assistants are thereby eliminated. The extension in at least two space directions provides the user with the option of applying various pivoting movements with only one hand and applying favourable leverages in the process.

The single-handed operation according to the invention by means of a single hand-grip makes it easier for the user to vary the position of the microscope while simultaneously using the other hand for other activities.

A second object on which the invention is based is thus to improve this problem. This object is achieved by creating a hand-grip which can be detached from the microscope body. Since the ergonomy and the speed during detachment are to be kept generous, it is preferred according to the invention to provide single-handed operation.

BRIEF DESCRIPTION OF THE DRAWINGS

The invention is to be explained in more detail by way of example with the aid of drawings, in which:

FIG. 4 shows a holding piece which can be fastened on a microscope housing;

FIG. 5 shows an oblique view of a hand-grip according to the invention;

FIG. 6 shows the comparable hand-grip according to FIG. 5, but seen from the microscope side;

FIG. 7 shows the hand-grip of FIG. 6 in an oblique side view in the premounting position;

FIG. 8 shows the hand-grip of FIG. 6 in an oblique rear view;

FIG. 9 shows the hand-grip of FIG. 6 in an oblique rear view with closed spindle, and FIG. 10 shows the hand-grip of FIG. 6 in an oblique front view.

DETAILED DESCRIPTION OF THE INVENTION

Figure 1:
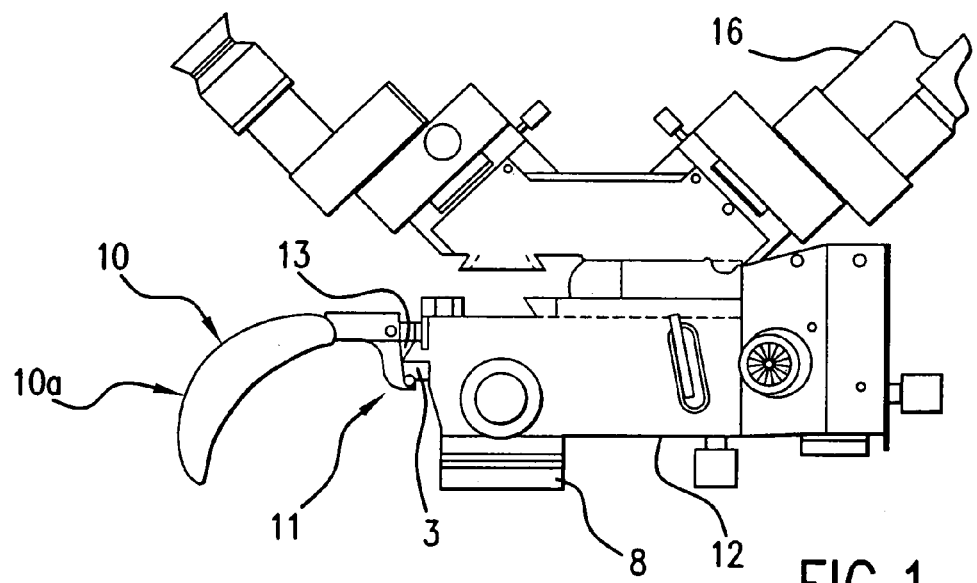
FIG. 1 shows a microscope as held, for example, pivotably on a stand, with a novel hand-grip.

Identical components bear the same reference numerals in the following description of the figures, while different components bear different reference numerals.

Different components having the same functions bear the same reference numerals with different indices.

The figures are described as a whole.

A microscope body 12 with a main objective 8 has at a central point a holding piece 3 which is constructed on the microscope body 12 or is permanently connected to the latter, for example by screws in fastening bores 15 (FIG. 6).

The holding piece 3 serves to a hold a mounting part 11 with the gripping part 10 of the novel hand-grip. A plurality of such holding pieces could be mounted on the microscope body or on the pivoted support 16 or on the stand or at other locations. The holding piece 3 has two bearing pins or a shaft 2 at the upper end of the holding piece 3, and a thrust bolt 5 at the lower end of the holding piece 3.

Both the shaft 2 and thrust bolt 5 and, if appropriate, also the external shape of the holding piece serve the purpose of holding a mounting device 13 of a mounting part 11 of the hand-grip. The mounting part is connected in one piece to a gripping part 10 which permits an operator to vary the position of the microscope.

The mounting device 13 comprises a vice-like spindle 4, which, for locking purposes, has a slot 7 which cooperates with the thrust bolt 5 and clamps the latter if the spindle is rotated about its axis. The slot 7 has for this purpose side walls which lock the thrust bolt 5 against the detaching direction in the mounted position. At the same time, however, the spindle 4 is mounted in a thread which is designed such that when the spindle 4 is rotated in the locking direction pressure is applied to the thrust bolt 5 in its axial direction, as a result of which the mounting part 11 clings to the holding piece 3. Provided for this purpose are two half bearings 1 aligned with the spindle 4 in the mounting device, which cooperate with the shaft 2 in the mounted position. They have for this purpose shell-shaped recesses 14 which can pivot about the shaft 2, as is illustrated in the comparison of FIG. 7 or FIG. 8.

FIG. 8 shows the spindle 4 in the state in which the slot 7 is ready to accept the thrust bolt 5, while FIG. 9 shows that spindle position in which the thrust bolt 5 is locked.

The spindle 4 can be operated by a clamping lever 6 which projects from the mounting device 13 in the direction of the gripping piece 10. In the exemplary embodiment, the clamping lever can be operated without a problem with a finger, for example with the thumb, in order to permit the spindle 4 to be locked or unlocked with the aid of the thrust bolt 5.

Locking operation:

The half bearing 1 of the mounting device 13 is mounted in a slightly inclined position from above onto the shaft 2 of the holding piece 3 and then pivoted slightly downwards to a stop such that the spindle 4 of the mounting device 13 comes to lie under the thrust bolt 5 of the holding piece 3. If the clamping lever 6 and, with it, the spindle 4 are rotated by approximately 90° in this position, the side walls of the slot 7 of the spindle 4 lock the thrust bolt 5, and the base surface of the slot 7 presses from below onto the thrust bolt 5. Consequently, on the one hand the half bearing 1 is pressed onto the shaft 2, and on the other hand a self-closure is produced with the thrust bolt 5, as a result of which the holding grip is fixed permanently on the holding piece 3.

Other elements (not illustrated) are also conceivable as spindles, for example eccentric cams, wedges, etc. The spindle 4 or the thrust bolt 5 can be sprung in order to compensate a travel or play, or tolerances—for example when the holding grip is to be mounted over a drape.

Figure 2:
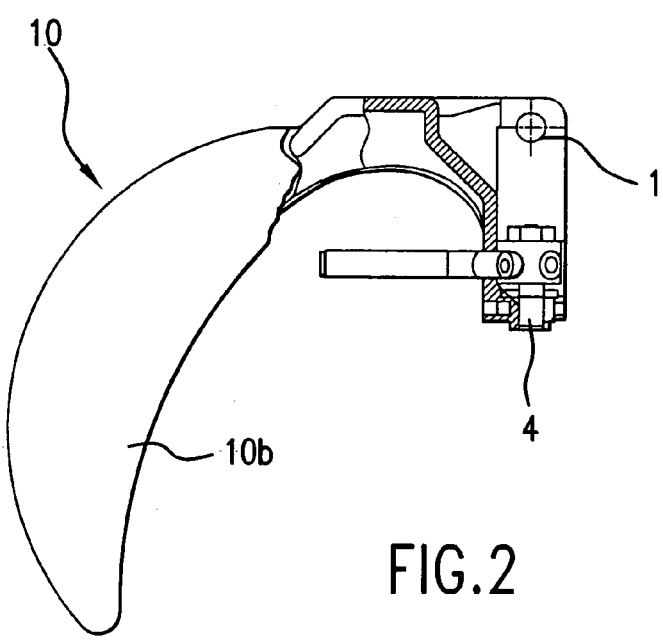
FIG. 2 shows a section along the line A—A of FIG. 3 of the novel hand-grip.
Figure 3:
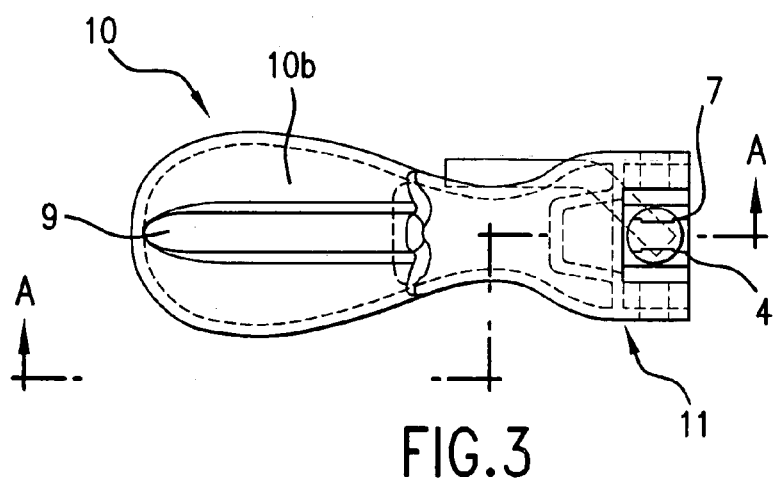
FIG. 3 shows a novel hand-grip in a view from above.

The gripping pieces 10*b* in accordance with FIG. 2–FIG. 5 differ from the remaining gripping pieces 10*a*, which are distinctively constructed in the shape of a banana with structured surface. The lightweight design of the gripping piece 10*b* provides a cutout 9 to lighten the weight and, as may be gathered from FIG. 2, is hollow.

As noted above, the present invention can include detachable single-handed grips. However, the invention is not limited to detachable single-handed grips. Rather, it also comprises variants with pairwise hand-grips which can be detached according to the invention individually or in common.

According to the invention, in the case of the detachable hand-grips a mounting part is constructed on the grip piece and cooperates with a holding piece or with a matching formation of the microscope housing.

Of course, the invention also comprises all interchanged formations (male exchanged with female).

According to the invention, all known detachable connecting mechanisms are available for the connection between hand-grip and microscope housing. The invention is not limited in that extent. What is decisive is the possibility of easy single-handed detachment of the connection mechanism. Mounting elements ale preferably applied as clamping levers, tommy levers, mounting screws or mounting nuts with steep threads or other elements which require only a few or only fractions of revolutions in order to lock or to unlock such as, for example: bayonet closure parts (male or female) or the like.

According to the invention, this comprises both variant solutions which require two fingers for operation or, in particular, also those which manage with one finger. Operation by means of the thumb is preferred in this case, because this finger can generally apply the greatest force.

Specific built-on accessories are advantageous in which use is made of clamping levers which in one position define the fixing, and in the other position define the detachment. Such clamping levers can be operated with particular speed and—when operated with the thumb—permit a high closing or detaching force.

Theoretically, single-point fastening suffices if the mounting part bears tightly against the microscope housing. However, in the case of one design, the invention preferably provides multipoint fastening in the case of which a latching point is provided in addition to a locking point. The latching point can have, for example, a latching pin or a shaft, which pin or shaft engages in matching recesses such that the grip part can be pivoted into the locking point after the connection of the latching point.

The invention also renders it possible to mount hand-grips over a drape. That is to say, a microscope, which cannot be optimally sterilized as a rule, can be fully protected through the drape, and a hand-grip which can be optimally sterilized is fitted thereover. In order to render this possible, in a particular design of the invention a sufficient travel (play) is provided between the mounting part of the hand-grip and the holding piece on the microscope housing.

In order to compensate tolerances, elastic or spring-loaded elements are provided in a particular design.

In one embodiment of the present invention, the hand grip has a grip portion with an antiadhesive (non-stick) and/or sterilizable surface or a surface that exhibits lotus blossom effect. These surfaces can be obtained by coating the hand grip with a substance that will provide an antiadhesive (non-stick) and/or sterilizable surface or a surface that exhibits lotus blossom effect.

The design of the grip according to the invention is based on the known setting of tasks and solutions, there being a novel addition of the possibility according to the invention of using the grip as a single-handed operating grip. That is to say, only one hand must be used, not only to detach and mount the grip, but also to guide the microscope. Consequently, it is advantageous when the grip is curved downwards, since this serves the purpose of ergonomic manipulation, and also the possibility of applying pivoting forces.

The hand-grip is preferably selectable from a range of differently shaped grips, in order to accommodate as far as possible the comfort of the respective operating staff. This has not so far been possible with permanently mounted grips.

In accordance with a further development, the hand-grip also comprises electric operating elements which can be connected to the circuits on the microscope housing via plug-in contacts in the region of the mounting part. These plug-in contacts are preferably integrated such that the electric connection is performed simultaneously with the mechanical connection.

The strength according to the invention of the novel concept comes to bear, in particular, when there is more than only one point on the microscope housing which serves for grip mounting, because the correct mounting site can be selected depending on what is required. This is the case even under conditions of an operation, where quick reactions and short changeover times are important.

The invention is not limited to self-closed or force-closed connections between the hand-grip and a microscope housing. Rather, pure clamping connections can also be used, as in which case satisfactory connecting forces can be applied by means of clamping friction or static friction. Detachment is performed, for example, in the case of such built-on accessories by a jerky movement.

A typical variant would be, for example, an adhesive connection by means of magnetic force which is applied in the form of permanent magnets or of electromagnets. Such electromagnets being switched on/off by means of electrical switches which do not need much of a switching force. Hence, it allows the removal and connection of the hand grip without imparting force on the microscope and without moving the microscope.

The invention and its variant developments can therefore be used to take better account of the requirements, for example, specifically in microsurgery, in ear, nose and throat surgery and in all other, including industrial, applications of microscopes.

PARTS LIST

1 Half bearing (part of a bearing for inserting a locking part)
2 Shaft
3 Holding piece
4 Spindle, vice-like
5 Thrust bolt
6 Clamping lever
7 Slot
8 Main objective
9 Cutout
10 Gripping piece
11 Mounting part
12 Microscope housing
13 Mounting device
14 Recess, shell-shaped
15 Assembly bore
16 Pivoted support

What is claimed is:

1. A microscope having a microscope housing and a single hand-grip with a grip part, wherein the hand-grip has a mounting device which is adapted to allow the hand-grip to be removed from the microscope housing by a single-handed movement or connected to the microscope housing by a single-handed mounting movement, and wherein the mounting device includes a movable locking member adapted to positively fix the hand-grip on the microscope when a portion of the movable locking member is moved to an opposite side of a portion of the microscope with respect to a direction of removal of the hand-grip.

2. The microscope according to claim 1, wherein the grip part is configured so that the centerline of the grip part extends in a two-dimensional curve when mounted on the microscope.

3. The microscope according to claim 2, wherein the grip part is curved.

4. The microscope according to claim 2, wherein the sides of the single hand-grip bisected by a plane on which the axis of the grip part lies are of a substantially mirror-image configuration.

5. The microscope according to claim 1, wherein the grip part is coated with a substantially non-stick material.

6. The microscope according to claim 5, wherein the coated grip part exhibits a lotus blossom effect.

7. The microscope according to claim 1, wherein the single hand-grip is constructed in a lightweight fashion as a hollow body.

8. The microscope according to claim 7, wherein the hand-grip is made from light metal or plastic.

9. The microscope according to claim 1, wherein the grip part is of banana-shaped construction.

10. The microscope according to claim 9, wherein the grip part is curved downwards when the hand-grip is mounted on the microscope.

11. The microscope according to claim 1, wherein the grip part is configured so that a portion of the axis of the grip part extends substantially in the horizontal direction and so that a portion of the axis of the grip part extends substantially in the vertical direction when mounted on the microscope.

12. The microscope according to claim 11, wherein the grip part is curved.

13. The microscope according to claim 11, wherein the sides of the grip part bisected by a plane on which the axis of the grip part lies are of a substantially mirror-image configuration.

14. The microscope according to claim 1, wherein the grip part is configured so that a portion of the axis of the centerline of the grip part extends in a two-dimensional curve when mounted on the microscope.

15. The microscope according to claim 14, wherein the grip part is curved.

16. The microscope according to claim 14, wherein the sides of the grip part bisected by a plane on which the axis of the grip part lies are of a substantially mirror-image configuration.

17. The microscope according to claim 1, wherein sides of the single hand-grip bisected by a plane on which the axis of the grip part lies are of a substantially mirror-image configuration.

18. The microscope according to claim 17, wherein the axis is curved.

19. The microscope according to claim 1, wherein sides of the grip part bisected by a plane on which the axis of the grip part lies are of a substantially mirror-image configuration.

20. The microscope according to claim 19, wherein the axis is curved.

21. The microscope according to claim 1, wherein the microscope body comprises a microscope housing wherein the substantially central point on the microscope body is also the substantially central point on the microscope housing, and wherein the single hand-grip is provided at the substantially central point on the microscope housing.

22. The microscope according to claim 1, wherein at least the grip part is constructed from antiadhesive material.

23. The microscope according to claim 22, wherein the grip part that is constructed from antiadhesive material exhibits a lotus blossom effect.

24. The microscope according to claim 1, wherein at least the grip part is coated with a sterilizable coating.

25. The microscope according to claim 1, wherein at least the grip part is constructed from a sterilizable material.

26. The microscope according to claim 1, wherein at least the grip part is coated with an antiadhesive and sterilizable coating.

27. The microscope according to claim 1, wherein at least the grip part is constructed from a material exhibiting antiadhesive and sterilizable properties.

28. The microscope according to claim 1, wherein the mounting device is further adapted to allow for removal and connection of the hand-grip while imparting substantially no force on the microscope.

29. The microscope according to claim 1, wherein the mounting device is further adapted to allow for removal and connection of the hand-grip without substantially moving the microscope.

30. The microscope according to claim 1, wherein the microscope is freely movable, and wherein the mounting device is further adapted to allow for removal and connection of the hand-grip without substantially moving the microscope.

31. The microscope according to claim 1, wherein the grip part is configured so that the centerline of the grip part extends in a three-dimensional curve when mounted on the microscope.

32. The microscope according to claim 1, wherein the grip part is configured so that a portion of the centerline of the grip part extends in a three-dimensional curve when mounted on the microscope.

33. A handle for a microscope, comprising:
a single hand-grip for a microscope having a microscope body on a pivoted support, wherein the hand-grip has a spatial extent in at least two space directions when mounted at a substantially central point on the microscope body, wherein the hand-grip is adapted to be mounted on the microscope body to allow an operator to vary the position of the microscope with respect to a stationary object being viewed with the microscope, wherein the hand-grip has a mounting device which is adapted to allow the hand-grip to be removed from the microscope body by a single-handed movement or connected to the microscope body by a single-handed mounting movement, and wherein the mounting device includes a movable locking member adapted to positively fix the hand-grip on the microscope when a portion of the movable locking member is moved to an opposite side of a portion of the microscope with respect to a direction of removal of the hand-grip.

34. The handle according to claim 33, wherein the hand-grip is adapted to be removed from the microscope body and fastened to the microscope body without tools.

35. The handle according to claim 33, wherein the hand-grip has a grip portion and at least the grip portion is coated to be antiadhesive.

36. The handle according to claim 35, wherein the coated grip portion exhibits a lotus blossom effect.

37. The handle according to claim 33, wherein the hand-grip is constructed in a lightweight fashion as a hollow body.

38. The handle according to claim 37, wherein the hand-grip is made from light metal or plastic.

39. The handle according to claim 33, wherein the hand-grip has a grip portion and at least the grip portion is constructed from antiadhesive material.

40. The handle according to claim 39, wherein the grip portion that is constructed from antiadhesive material exhibits a lotus blossom effect.

41. The handle according to claim 33, wherein the hand-grip has a grip portion and at least the grip portion is coated with a sterilizable coating.

42. The handle according to claim 33, wherein the hand-grip has a grip portion and at least the grip portion is constructed from a sterilizable material.

43. The handle according to claim 33, wherein the hand-grip has a grip portion and at least the grip portion is coated with an antiadhesive and sterilizable coating.

44. The handle according to claim 33, wherein the hand-grip has a grip portion and at least the grip portion is constructed from a material exhibiting antiadhesive and sterilizable properties.

45. The handle according to claim 33, wherein the hand-grip has a grip portion which is banana-shaped.

46. The handle according to claim 45, wherein the grip portion is curved downwards when the hand-grip is mounted on the microscope.

47. The handle according to claim 33, wherein the mounting device is further adapted to allow for removal and connection of the hand-grip without substantially moving the microscope.

48. The handle according to claim 33, wherein the microscope is freely movable, and wherein the mounting device is further adapted to allow for removal and connection of the hand-grip without substantially moving the microscope.

* * * * *